US00PP08498P

United States Patent [19]

Bradford et al.

[11] Patent Number: Plant 8,498

[45] Date of Patent: Dec. 14, 1993

[54] PLUM TREE (BRADGREEN)

[76] Inventors: Lowell G. Bradford, 12439 E. Savana Rd.; Norman G. Bradford, 11875 E. Savana Rd., both of Le Grand, Calif. 95333

[21] Appl. No.: 999,786

[22] Filed: Dec. 28, 1992

[51] Int. Cl.[5] ..... A01H 5/00

[52] U.S. Cl. ..... Plt./68.1

[58] Field of Search ..... Plt./38.1, 38.2

[56] References Cited

U.S. PATENT DOCUMENTS

P.P. 3,617 9/1974 Anderson ..... Plt. 38.1

*Primary Examiner*—James R. Feyrer

[57] ABSTRACT

The present invention relates to a plum tree and more particularly to a new and distinct variety broadly characterized by a medium size, vigorous, and medium productive tree, which requires cross pollinization. The fruit matures under the ecological conditions described in mid August, with first picking on Aug. 3, 1992, and the last picking on Aug. 18, 1992. The fruit is uniformly medium in size, clingstone in type, shiny green in skin color, attractively oblate in shape, exceptionally sweet in flavor, very crisp in texture, and excellent in keeping and shipping quality. The variety was developed as a second generation open pollinated seedling of Black Beaut (U.S. Plant Pat. No. 3,617).

1 Drawing Sheet

BACKGROUND OF THE NEW VARIETY

In a continuing effort to improve the quality of shipping fruits, we, the inventors, typically hybridize a large number of nectarine, peach, plum, apricot, and cherry seedlings each year. The present invention relates to a new and distinct variety of plum tree, which has been denominated varietally as "Bradgreen". Each year we grow a large number of seeds from selected seed parents that have been hybridized by selected pollen parents. We also grow a large number of seeds from selected seed parents that were open pollinated by unknown pollen sources. The present variety was developed by us in 1985, and the resulting seedling was planted in a cultivated area of our experimental orchard at Bradford Farms near Le Grand, Calif. in Merced County (San Joaquin Valley). Specifically, this seedling was originated by growing an open pollinated seed of an unnamed seedling, this unnamed seedling being an open pollinated seedling of Black Beaut (U.S. Plant Pat. No. 3,617). Subsequent to origination of the present variety of plum tree, we asexually reproduced it by budding and grafting, and such reproduction of plant and fruit characteristics were true to the original plant in all respects.

The present variety is similar to its grandparent, Black Beaut (U.S. Plant Pat. No. 3,617), by being self-sterile and by producing fruit that is medium in size, but is very different therefrom by producing fruit that ripens about 60 days later, that is substantially better in flavor, and that is green in skin color, rather than black.

The present variety is most similar to Kelsey (unpatented) by producing late season fruit that is green in skin color, but is distinguished therefrom and an improvement thereon by producing fruit that matures two to three weeks later, that is firmer and crisper in texture, that is substantially sweeter in flavor, and that has a perfectly rounded apex, instead of a protruding tip.

DRAWING

The accompanying photograph exhibits five whole fruits positioned to display the characteristics of the skin color and form; one fruit divided transversely to its axial diameter to reveal the flesh and stone; and several leaves, all typical of the subject variety.

POMOLOGICAL CHARACTERISTICS

Referring now more specifically to the pomological characteristics of this new and distinct variety of plum tree, the following has been observed under the ecological conditions prevailing at the experimental orchard of the inventors near Le Grand, Merced County, (San Joaquin Valley), Calif. All major color code designations are by reference to the Inter-Society Color Council, National Bureau of Standards. Common color names are also used occasionally.

TREE

Size: Medium.
Vigor: Vigorous.
Growth: Spreading and dense.
Form: Vase formed.
Hardiness: Hardy.
Production: Medium productivity.
Bearing: Regular bearer.
Trunk:
- *Size.*—Medium.
- *Texture.*—Shaggy.
- *Bark color.*—Dark grayish brown [62. d.gy.Br].
- *Lenticels.*—Numerous. Color: Strong yellowish brown [74. s.yBr]. Size: ¼" to ⅜" [6.4–9.5 mm.].

Branches:
- *Size.*—Medium.
- *Texture.*—Smooth.
- *Color.*—1st Year Wood: Vivid yellow green [115. v.YG]. Older Wood: Light yellowish brown [76. l.yBr].
- *Lenticels.*—Numerous, very small. Color: Strong orange yellow [68. s.OY]. Average Size : 1/16" [1.6 mm.].

Leaves:
- *Size.*—Small. Average Length: 2⅞" [73.0 mm.]. Average Width: 1½" [38.1 mm.].
- *Thickness.*—Medium.
- *Form.*—Elliptical.

*Apex.*—Acuminate.
*Base.*—Acute.
*Surface.*—Smooth.
*Color.*—Dorsal Surface: Moderate olive green [125. m.OlG]. Ventral Surface: Moderate yellowish green [136. m.yG].
*Margin.*—Finely serrate.
*Venation.*—Pinnately net veined.
*Petiole.*—Average Length: ½" [12.7 mm.]. Average Thickness: 1/16" [1.6 mm.]. Color: Vivid yellow green [115. v.YG] with some grayish yellowish pink [32. gy.yPk] when exposed to sunlight.
*Stipules.*—Numerous. Average Length: 7/32" [5.6 mm.].
*Glands.*—Number: 1 or 2 per leaf. Position: Opposite on base of blade when paired. Size: Small. Form: Globose. Color: Strong yellow green [117. s.YG].

Flower buds:
*Hardiness.*—Half hardy.
*Size.*—Medium.
*Length.*—Medium.
*Form.*—Free.
*Surface.*—Pubescent.

Flowers:
*Blooming period.*—Early as compared with other varieties.
*Size.*—Medium.
*Color.*—White [263. White].

FRUIT

Maturity when described: Hard but eating ripe, Aug. 13, 1992. However, in 1992 practically all stone fruit varieties matured from 12 to 17 days earlier than normal, so it should be expected that the present variety would harvest between August 15 and September 3 during normal years.
Date of first picking: Aug. 3, 1992.
Date of last picking: Aug. 20, 1992.
Size: Uniform, medium.
*Average diameter axially.*—2⅛" [54.0 mm].
*Average traversely in suture plane.*—2⅜" [60.3 mm].
Form: Uniform, very symmetrical, ellipsoidal.
*Longitudinal section form.*—Slightly oblate.
*Transverse section through diameter.*—Round.
Suture: An inconspicuous shallow line extending from the base, but discontinuing at the apex.
Ventral Surface: Rounded.
Lips: Virtually none.
Cavity: Flaring, circular, with the suture showing on one side only.
Base: Slightly truncate and slightly cuneate.
Apex: Rounded.
Pistil point: Apical, negligible in length.
Stem: Small.
*Average length.*—¼" to ⅜" [6.4–9.5 mm.].
*Average width.*—1/16" [1.6 mm.].

Skin:
*Thickness.*—Medium.
*Texture.*—Medium.
*Tenacity.*—Tenacious to flesh.
*Tendency to crack.*—Slight in wet season.
*Color.*—Strong yellow green [117. s.YG] blending to deep greenish yellow [100. deep gY] with some pale yellow [89. p.Y] freckling more prominent toward the apex and with some moderate red [15. m.R] blushing near the base or where exposed to the sun.
*Blush.*—Abundant.

Flesh:
*Color.*—Light yellow green [119. l.YG] near the skin smoothly blending to pale yellow green [121. p.YG] near the stone.
*Amygdalin.*—Moderate.
*Juice.*—Abundant, rich.
*Texture.*—Firm, tough, very crisp.
*Fibers.*—Abundant, fine, tender.
*Ripens.*—Evenly.
*Flavor.*—Very sweet with medium acidity.
*Aroma.*—Moderate.
*Eating quality.*—Excellent, even if picked prematurely.
*Average brix on Aug.* 3, 1992.—19
*Average brix on Aug.* 18, 1992.—24

STONE

Type: Clingstone.
Form: Oval.
Base: Oblique.
Apex: Rounded.
Sides: Equal.
Surface: Rugose, with grooves on each side of the dorsal fin.
Color: Light yellowish brown [76. l.yBr].
Average width: 11/16" [17.5 mm.].
Average length: 13/16" [20.6 mm.].
Average thickness: ⅜" [9.5 mm.].
Average pit wall thickness: 1/16" [1.6 mm.].
Tendency to split: None observed.
Kernel:
*Form.*—Oval.
*Taste.*—Bitter.
*Viable.*—Yes.
*Average width.*—7/16" [11.1 mm.].
*Average length.*—9/16" [14.3 mm.].
*Color.*—Pale yellow [89. p.Y] when freshly removed.
Pellicle color: Light grayish brown [60. l.gy.Br].
Amygdalin: Abundant.

USE

Market: Fresh and long distance shipping.
Keeping quality: Excellent.
Shipping quality: Excellent.
Resistance to insects: No unusual susceptibilities noted.
Resistance to diseases: No unusual susceptibilities noted.

Although the new variety of plum tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

We claim:

1. A new and distinct variety of plum tree, substantially as illustrated and described, broadly characterized by a medium size, vigorous, and medium productive tree, which requires cross pollinization to produce late season fruit that is similar to that of Kelsey (unpatented) by being green in skin color, but is distinguished therefrom and an improvement thereon by producing fruit that matures two to three weeks later, that is firmer and crisper in texture, that is substantially sweeter in flavor, and that has a perfectly rounded apex, instead of a protruding tip.

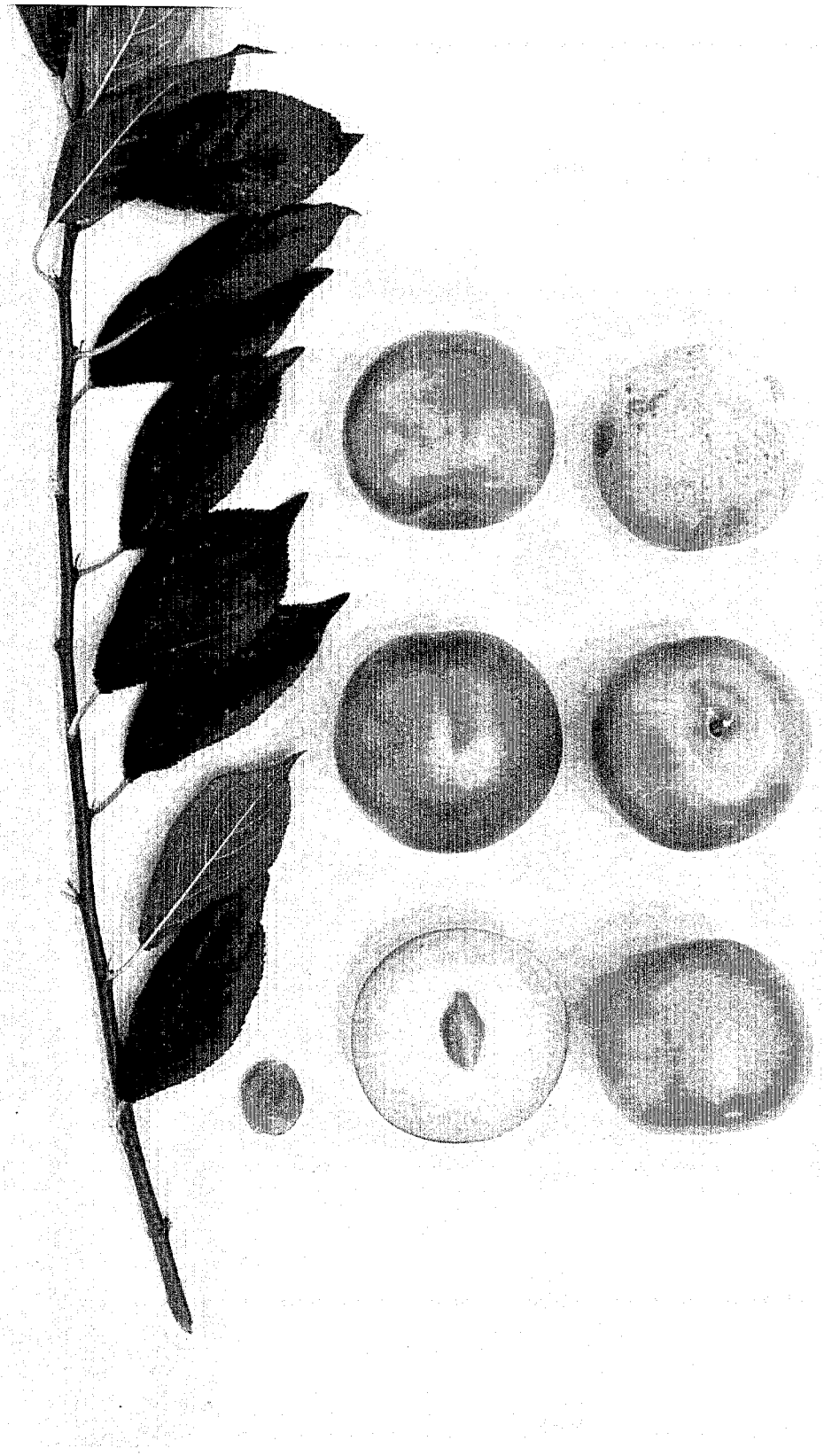

* * * * *